United States Patent [19]
Kim et al.

[11] Patent Number: 6,113,859
[45] Date of Patent: *Sep. 5, 2000

[54] BAR-TYPE $NO_x$ GAS SENSOR HAVING $WO_3$ SENSING FILM

[75] Inventors: Tae Song Kim; Hyung Jin Jung; Chong Hak Jung, all of Seoul, Rep. of Korea

[73] Assignee: Korea Institute of Science and Technology, Rep. of Korea

[*] Notice: This patent issued on a continued prosecution application filed under 37 CFR 1.53(d), and is subject to the twenty year patent term provisions of 35 U.S.C. 154(a)(2).

[21] Appl. No.: 09/018,802

[22] Filed: Feb. 4, 1998

[51] Int. Cl.[7] ...................................................... G01N 27/12
[52] U.S. Cl. ................................................ 422/90; 422/98
[58] Field of Search ................................. 422/90, 94, 98; 436/116, 118; 338/34

[56] References Cited

U.S. PATENT DOCUMENTS

| | | | |
|---|---|---|---|
| 4,935,289 | 6/1990 | Kikuchi et al. | 428/209 |
| 5,389,340 | 2/1995 | Satake | 422/98 |
| 5,624,640 | 4/1997 | Potthast et al. | 422/90 |

FOREIGN PATENT DOCUMENTS

| | | |
|---|---|---|
| 6-148113 | 5/1994 | Japan . |
| 9510774 | 4/1995 | WIPO . |

*Primary Examiner*—Jeffrey Snay
*Attorney, Agent, or Firm*—Morrision & Foerster

[57] ABSTRACT

A plate-type $NO_x$ gas sensor having a $WO_3$ sensing film which are capable of preventing temperature variation of a sensing thin film depending on gas flow to decrease heat loss thereof, whereby extending the life span of batteries of a portable gas sensor. The plate-type $NO_x$ gas sensor includes a Pt thin film electrode formed on a front surface of an alumina substrate, a tungsten oxide thin film for sensing $NO_x$ gas deposited on the front surface of the substrate on which the Pt thin film electrode is formed, a heater formed on a back surface of the alumina substrate for holding a portion of the tungsten oxide thin film for sensing $NO_x$ gas within a predetermined temperature range, a conducting wire for connecting between the Pt thin film electrode and the heater and a sheet made of at least one material selected from a group composed of $Al_2O_3$, mullite, codierite, magnesia and zirconia, coated on the back surface of the substrate on which the heater is formed, for burying completely the heater from an exterior atmosphere to protect the heat dissipation. The $NO_x$ gas sensor may be fabricated as a bar type and also have a catalytic layer on the sensing layer to enhance the sensing characteristics of the sensor.

5 Claims, 8 Drawing Sheets

BAR-TYPE $NO_x$ GAS SENSOR HAVING $WO_3$ SENSING FILM

BACKGROUND OF THE INVENTION

1. Field of the Invention

The present invention relates to a $NO_x$ gas sensor having a $WO_3$ sensing film and a fabrication method thereof, and in particular which is fabricated in a thin film form so as to sense the density of $NO_x$ gas accurately by a semiconductor type based on a variation of an electrical conductivity.

2. Description of the Conventional Art

In the past, smokes from factory and heating fuel were the main cause of air pollution. Recently, gases exhausted from vehicles has been a serious cause of air pollution. Among the gases exhausted from vehicles, HC, CO and $O_x$ are harmful to humans. A photovolataic decomposition of $NO_x$ by a solar irradiation generated ozone($o_3$), which causes global warming and causes acid rain.

There are two kinds of $NO_x$ gases, one is exhausted from vehicles and the other exists naturally in the air. Since $NO_x$ gas is very harmful to the human beings, the American Conference of Governmental Industrial Hygienists(ACGIH) set a threshold limit value-time weighted average (TLV-TWA), which is the recommended reference value of $NO_x$ gas for the safety of human being, up to 25 ppm of NO and up to 3 ppm of $NO_2$.

Therefore, it is necessary to detect accurately $NO_x$ gas of low density more than 1 ppm. The conventional $NO_x$ gas density measuring methods employed an electrochemical sensor, a mass spectrometry, etc.

The conventional $NO_x$ gas sensor, however, has disadvantages in that it is difficult to install the gas sensor consistently in a portion of the unit which generates gases, such as in a vehicle, and it is difficult to miniaturize the gas sensor so as to transport the gas sensor easily to a position where the gas generation unit is placed. In addition, the fabrication cost thereof is high.

The semiconductor type gas sensor, apart from an electrochemical sensor and a mass spectrometry using an expensive apparatus and analyzer, utilizes an oxide semiconductor thin film. When gaseous molecules are adsorbed on a surface of the thin film, a transfer of electrons occurs between the semiconductor thin film and the adsorbed molecules. When an electron receiving gases, i.e., which is an oxidizing gases such as $NO_x$ gas are adsorbed, a carrier density of electron in the oxide semiconductor thin film is decreased and thus decreases an electrical conductivity thereof to increase the resistance value thereof. Therefore, the sensor, using an oxide (such as $WO_3$) thin film which has a n-type oxide semiconducting characteristics, is an excellent sensor which shows a sharp increase of resistance because of the electrical conductivity variation characteristics ($\sigma P_{o2}^{-1/2}$) in accordance with an oxygen partial pressure variation and a phenomenon of a reduction of the electrical conductivity at the time of adsorption of the oxidizing gases on the $WO_3$ thin film surface thereof.

Thus, the semiconductor type gas sensor has an excellent durability and also makes it possible to minimize the gas sensors.

However, the efficiency of gas adsorption must be optimized in order to use the variation of resistance as mentioned above. Thus, the sensing film should be held at an appropriate temperature, and this requires a heater placed around a portion of the sensing film in order to heat the film. Miniaturization is an advantage of the semiconductor type gas sensor, however, the emitting heat must be minimized because heat affects the life span of batteries of a portable gas sensor. Also, it is important to control the temperature of the sensor varied depending on gas flow in order to accurately measure the amount of gases in the portion in which there exists a flow of vehicle's exhausted gases.

Furthermore, the conventional semiconductor type gas sensor has disadvantages in that unless the electron transfer occurs rapidly when $NO_x$ gas is adsorbed on the surface of the sensing thin film it is difficult to accurately detect amount of gas, and an extended waiting time is required for repetitive measurements.

SUMMARY OF THE INVENTION

Accordingly, it is an object of the present invention to provide a $NO_x$ gas sensor having a $WO_3$ sensing film which makes it possible to miniaturize a high sensitive $NO_x$ gas sensor at a low cost, and which is well applicable in measuring gases exhausted from vehicles.

It is a further object of the present invention to provide a $NO_x$ gas sensor having a $WO_3$ sensing film which has an improved sensor structure which is capable of preventing temperature variation of the sensing thin film depending on gas flow and to decrease heat loss thereof, whereby extending the life span of batteries of a portable gas sensor.

To achieve the above objects, there is provided a plate-type $NO_x$ gas sensor having a $WO_3$ sensing film, which includes a Pt thin film electrode formed on a front surface of an alumina substrate, a tungsten oxide thin film for sensing $NO_x$ gas deposited on the front surface of the substrate on which the Pt thin film electrode is formed, a heater formed on a back surface of the alumina substrate for heating other side tungsten oxide thin film for sensing tungsten oxide thin film for sensing $NO_x$ gas within a predetermined temperature range, and a sheet made of at least one material selected from a group composed of $Al_2O_3$, mullite, codierite, magnesia and zirconia, coated on the back surface of the substrate on which the heater is formed, for burying completely the heater from an exterior atmosphere to protect the heat dissipation or temperature fluctuation due to small mass, and a method for fabricating thereof.

To achieve the above objects, there is also provided a bar-type $NO_x$ gas sensor having a $WO_3$ sensing film, which includes an alumina bar made of at least one material selected from a group composed of alumina, mullite, cordierite, magnesia and zirconia, a heater formed on the bar, also a sheet made of one of the above materials for burying completely the heater from an exterior atmosphere to protect the heat dissipation, a Pt thin film electrode formed on the sheet in a predetermined pattern, a tungsten oxide thin film for sensing $NO_x$ gas deposited on the sheet on which the Pt thin film electrode is formed and the heater, and a method for fabricating thereof.

To achieve the above objects, there is also provided a $NO_x$ gas sensor having a $WO_3$ sensing film, which includes a Pt thin film electrode formed on a front surface of an alumina substrate, a palladium-silver W thick film heater formed on a back surface of the alumina substrate, a conducting wire for connecting the Pt thin film electrode and the thick film heater, a tungsten oxide thin film for sensing $NO_x$ gas deposited on the front surface of the substrate on which the Pt thin film electrode is formed, a catalytic layer deposited on the tungsten oxide thin film and an heat-proof alumina adhesive material coated on the back surface of the substrate on which the heater is formed to insulate the substrate.

Additional advantages, objects and features of the invention will become more apparent from the description which follows.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIGS. 3A, 3B and 3C are graphs illustrating sensitivity variations based on gas density variation in a $NO_x$ gas sensor, of which:

FIG. 3A is a graph illustrating a sensitivity variation with respect to $NO_x$ gas density wherein a catalytic layer is not provided therein and an adhesive material is thin coated on a heater to expose the heater to air;

FIG. 3B is a graph illustrating a sensitivity variation with respect to $NO_X$ gas density wherein a heater is buried completely in sheets;

FIG. 3C is a graph illustrating a sensitivity variation with respect to $NO_x$ gas density wherein a catalytic layer is provided therein; and FIGS. 4A and 4B are graphs illustrating a variation of a response characteristics of a $NO_x$ gas sensor depending on time in each gas density, of which:

FIG. 4A is a graph illustrating a variation of a response characteristics depending on time in each $NO_x$ gas density wherein a catalytic layer is not provided; and FIG. 4B is a graph illustrating a variation of a response characteristics depending on time in each $NO_x$ gas density wherein a catalytic layer is provided.

DETAILED DESCRIPTION OF THE INVENTION

Figure 1A:
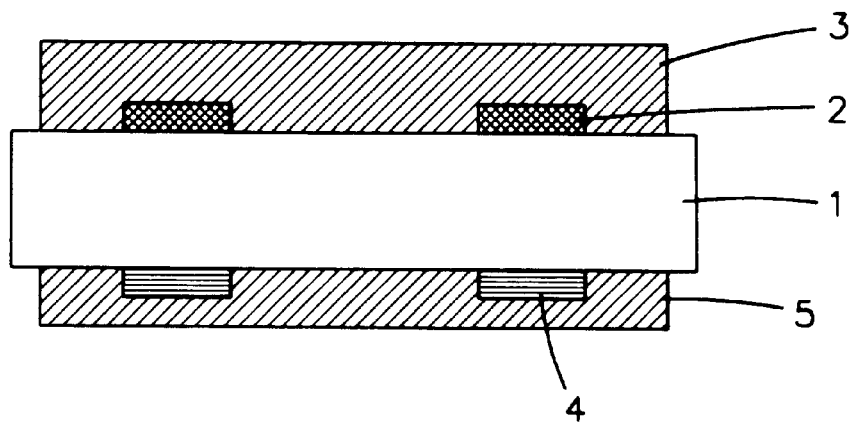
FIG. 1A is a cross-sectional view illustrating a conventional $NO_x$ gas sensor wherein a catalytic layer is not provided therein and an adhesive material is thin coated on a heater to expose the heater to air.

FIG. 1A illustrates a type of a conventional sensor, as shown therein, a heater 4 and a sensing film 3 are deposited on front and back surfaces, respectively, of an alumina substrate 1. The heater 4 on the back surface of the substrate 1 is externally exposed or thinly coated with a heatproof alumina adhesive 5, thus heat-emission can occurred easily. That is, according to the conventional sensor, the heater deposited on the back surface of the substrate is exposed air, or coated with a specific material not for heat-protection but for insulation.

Figure 1B:
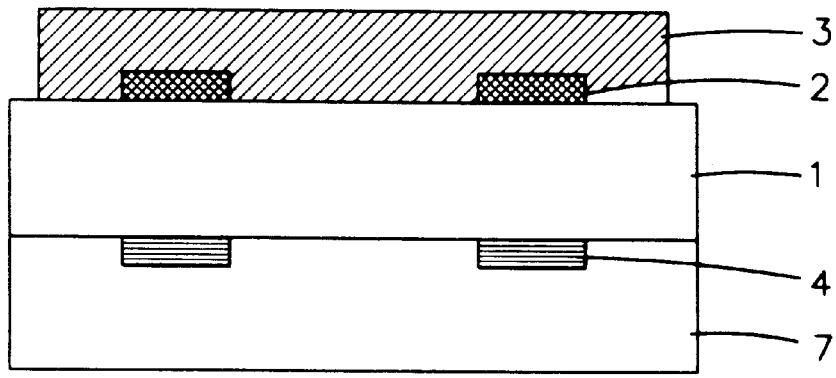
FIG. 1B is a cross-sectional view illustrating a plate-type $NO_x$ gas sensor according to the present invention wherein a heater is buried completely between alumina sheets.
Figure 1C:
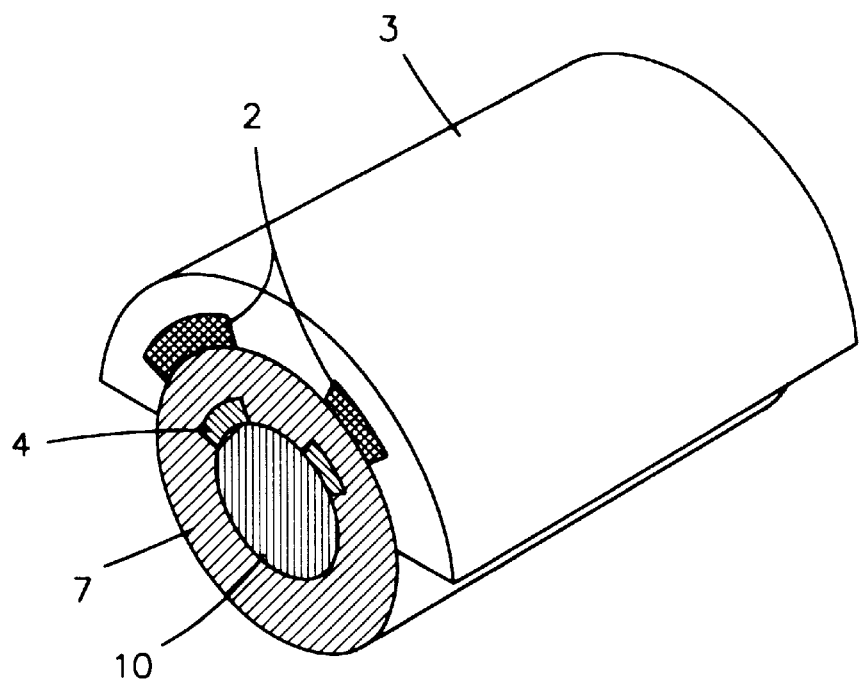
FIG. 1C is a cross-sectional view illustrating a bar-type $NO_x$ gas sensor according to the present invention wherein a heater is buried completely between an alumina bar and an alumina sheet which winds around the alumina bar.

On the other hand, FIG. 1B and 1C illustrate plate-type and bar type sensors according to one of the preferred embodiments of the present invention. As shown therein, a heater 4 is completely buried in an alumina sheet 7, thus improving a heat-protection effect. Namely, as shown in FIG. 1B illustrating the plate-type sensor, the heater 4 is placed in between a pair of alumina plates 1, 7. Also, according to the bar type sensor as shown in FIG. 1C, the heater 4 is inserted between an alumina bar 10 and an alumina sheet 7 which is wound the alumina bar 10.

As a heat-protection/insulation material, alumina ($Al_2O_3$), mullite, cordierite, magnesia (MgO), or zirconia ($ZrO_2$), etc. can be applied, as it is genarally known. Now, alumina will be illustrated as an example.

Pd/Ag or Pt/Au paste was applied to a conventional heater material. However, tungsten (W) paste can also be applied to the heater of the sensor according to the present invention.

Conventionally, since a coated layer serving as a heat-protection or an insulation of the heater was thinly applied or did not exist, the heater was easily exposed to air. Therefore, the Pd/Ag or Pt/Au paste, though high-priced, was applied to the conventional heater material because when W was applied as the material of the heater, efficiency of the heater dropped due to the oxidation of the heater under air atmosphere. However, since the heater according to the present invention is completely buried in the heat-protecting sheet, the oxidation of the heater will not occurred, thus the tungsten W, which is comparatively low-priced, can be applied as the material of the heater.

Figure 1D:
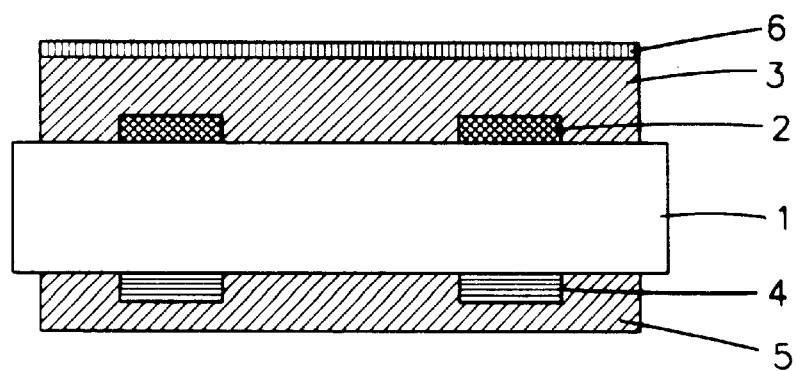
FIG. 1D is a cross-sectional view illustrating a $NO_x$ gas sensor according to the present invention wherein a catalytic layer is provided on a sensing film.

Furthermore, FIG. 1D illustrate a sensor having a catalytic layer 6 on a sensing film 3 in order to enhance the sensing characteristics of the sensor according to one of the preferred embodiments of the present invention.

EXAMPLES

Example 1

A fabrication method for a sensor including a completely-buried heater will now be described.

First, in a plate-type sensor having the completely-buried sensor, it is important to prepare alumina paste having a predetermined composition. The alumina paste was prepared by mixing alumina powder (AKP 30) no less than 60% and $SiO_2$, CaO powder no less than 0.1 wt % with PVB 79 of about 10% and diebutyl putalate (DBP) of about 10% as a binder, and then a solvent wherein methyl ethyl keton (MEK) and ethanol were in the ratio of 60:40 was added thereto, and a ball milling was performed for 48 hours, for thus preparing a paste which had a viscosity of 10,000 cps and thereafter the solvent was evaporated while mixing the paste by a stirrer in a decicator, thereby obtaining a resultant paste having a viscosity of 15,000–18,000 cps, and then a green sheet at thickness of at least 1 mm was formed by applying a doctor blade method. Then, the green sheet was dried for a day at room temperature, and a heater was formed on the green sheet by printing W paste by using a screen printing method. A heater was buried completely by overlaying the other green sheet on the heater, and an isostatic pressing process and a sintering process were applied thereto for tighter attachment therebetween. Here, a platinum electrode and a sensing film may be formed, before or after the sintering process is performed at about 1200–1500° C. Also, in order to control the temperature more accurately, a fine thermocouple may be attached adjacent to the sensing film.

Second, in a bar-type sensor having a completely-buried heater, a fabrication method of a sheet which winds around the bar was prepared in the same method as that of the plate-type sensor. A W paste serving as the heater was printed on front and rear surfaces of the sheet in accordance with a predetermined pattern, and the sheet were wound around the bar which had the same material as the sheet so as to bury the heater completely. An isostatic pressing process was applied for tighter attachment therebetween and a sintering process was performed at 1200–1500° C. Here, the bar can be fabricated by an extruding or a slip casting to have a diameter of approximately 5–10 mm. As like the plate-type sensor, the fine thermocouple may be applied to the bar-type sensor, and the sensing film may be deposited before or after the sintering process.

Figure 2:
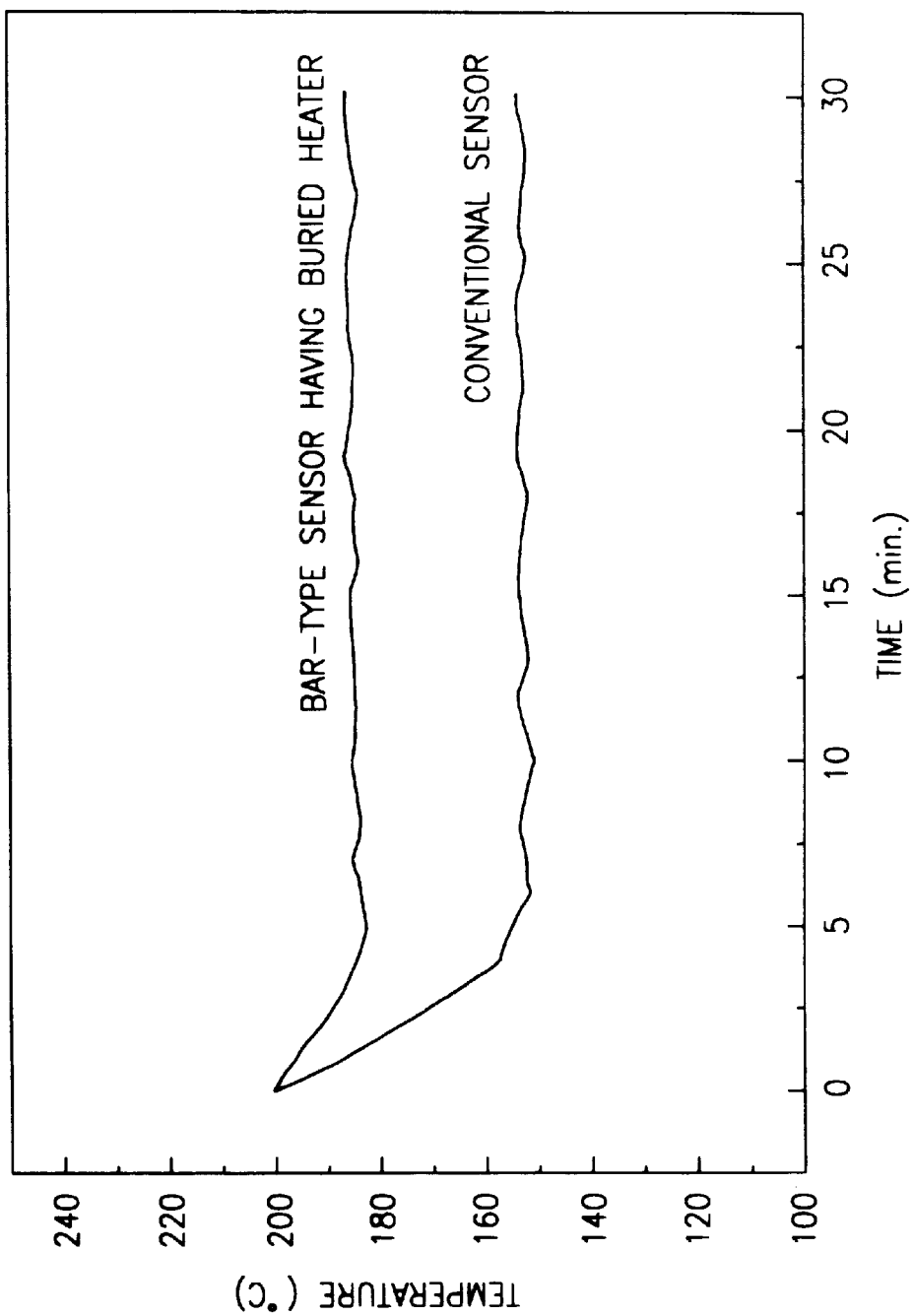
FIG. 2 shows a temperature variation decreased by a exhaust gas flow in a exhaust gas outlet when a conventional sensor and a bar-type sensor according to the present invention are applied to a vehicle exhaust gas outlet in order to examine the amount of heat loss when a heater is exposed to air.

FIG. 2 illustrates the result of temperature variation decreased by an exhaust gas flow in an exhaust gas outlet when the conventional sensor and the bar-type sensor according to one of the embodiment of the present invention were applied to a vehicle exhaust gas outlet in order to examine the amount of heat loss when the heater was exposed to air. As shown therein, when applying the bar-type sensor according to the present invention thereto, the temperature decreased about 37% less than the conventional sensor, which indicates that the bar-type sensor according to the present invention considerably reduced the temperature.

The change of sensitivity with respect to $NO_x$ gas concentration in the semiconductor-type gas sensor with the completely-buried heater and the semiconductor-type gas sensor with the exposed heater was as follows:

As a sensing thin film, a $WO_3$ film was applied to the both types of sensors by a DC sputtering method. The sensing film was deposited by the DC sputtering method by using a tungsten metal target at a thickness of approximately 3000 Å and maintaining a substrate at a temperature of 500° C. under oxygen atmosphere of 20% and thereafter the resultant was heat-processed at a temperature of 600° C.

Figure 3A:
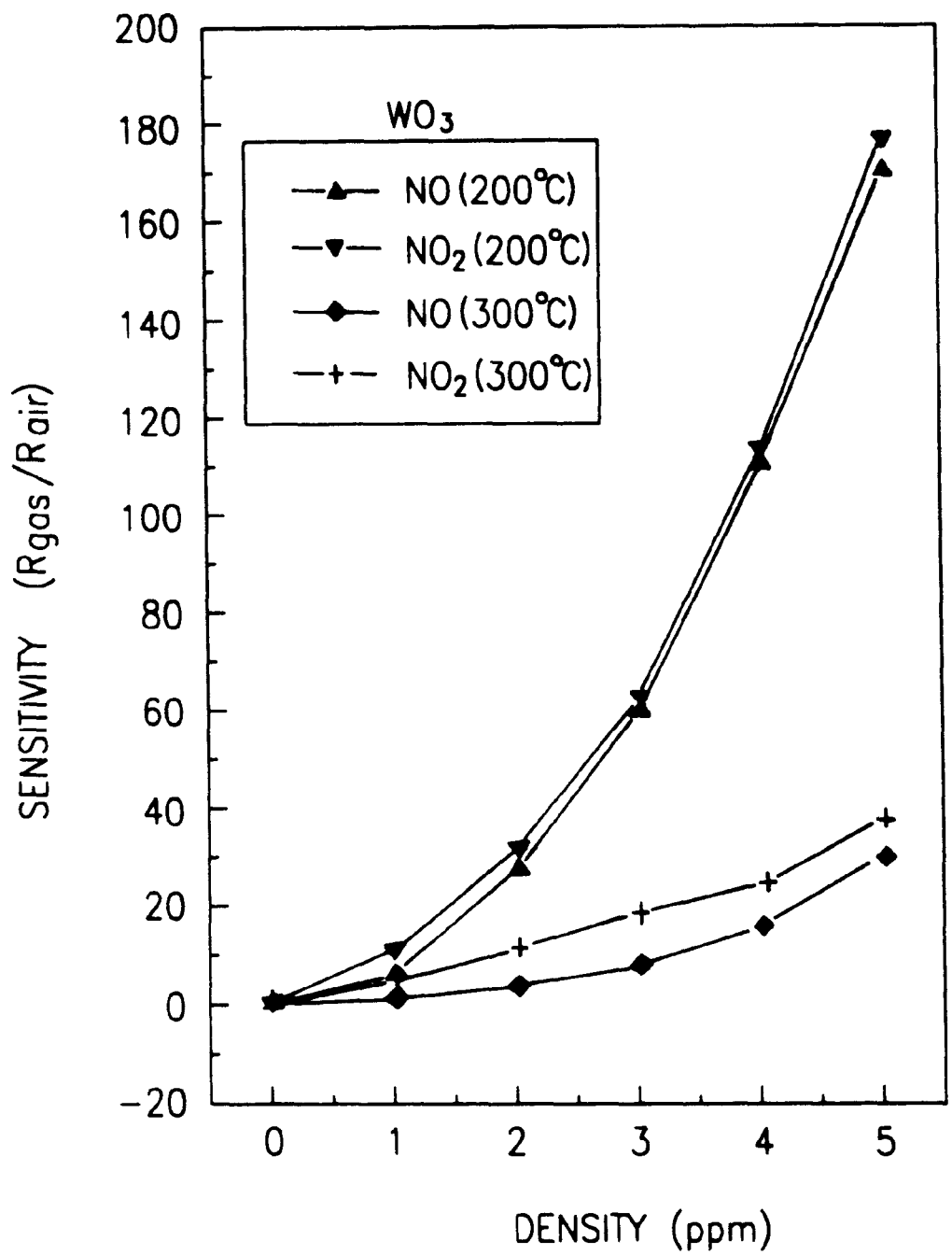
Figure 3B:
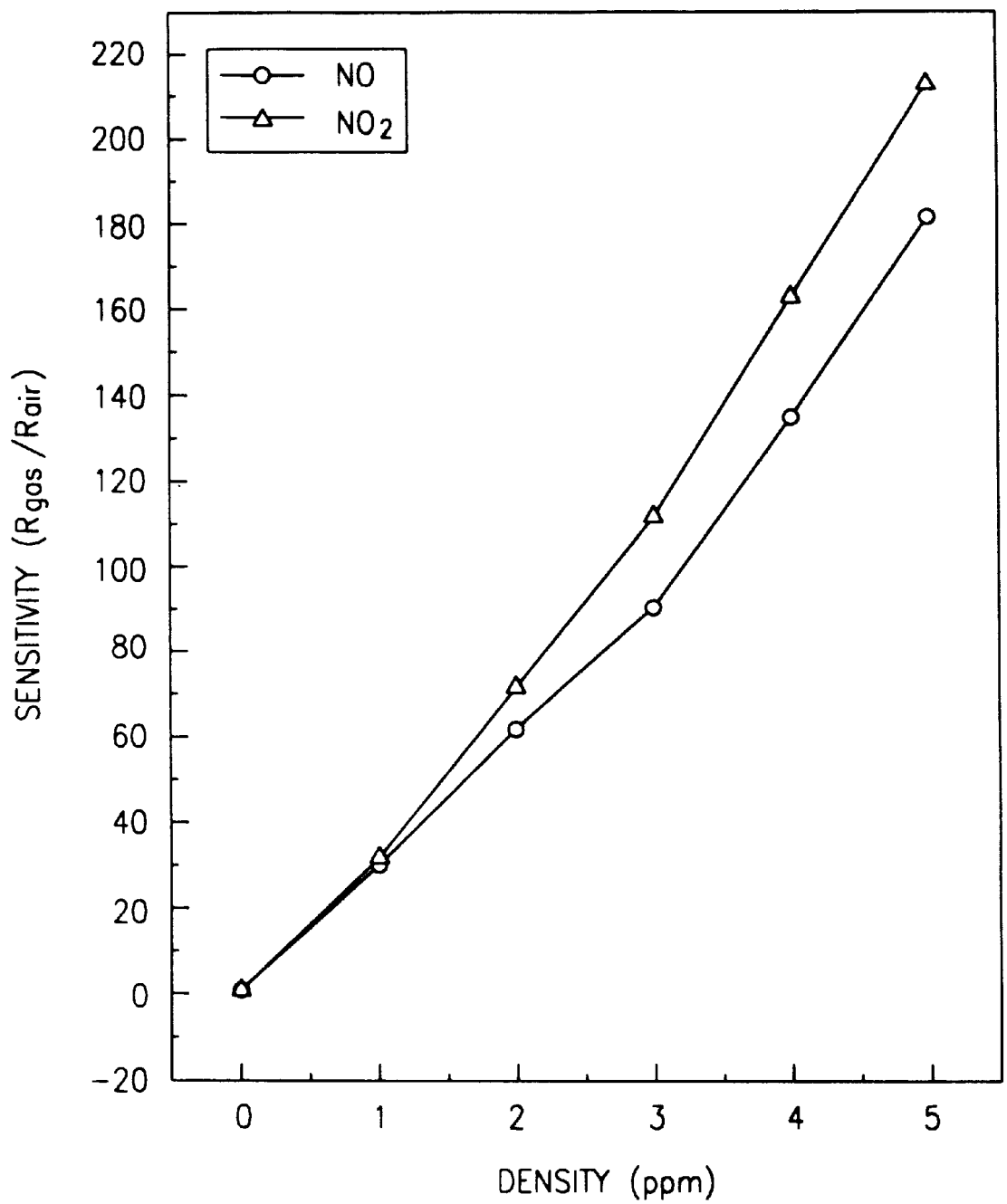

FIG. 3A illustrates the change of sensitivity with respect to $NO_x$ gas concentration of the conventional plate-type sensor having the exposed heater, and FIG. 3B illustrates the change of sensitivity with respect to $NO_x$ gas concentration of the bar-type sensor having the completely-buried heater according to the present invention. Both sensors show excellent sensitivity which was above 170 when the $NO_x$ gas concentration was 5 ppm. However, the bar type sensor having the completely-buried heater according to the present invention illustrates higher sensitivity than the conventional sensor.

Example 2

A fabrication method of $NO_x$ gas sensor according to the present invention was directed to depositing a Pt thin film having a thickness of a few thousands Å on an alumina substrate 1, at a room temperature by a sputtering method. After the Pt thin film was deposited, the resultant was heat-processed for 2~6 hours at a temperature of 600~750° C. under nitrogen environment by using a tube furnace in order to homogenize and stablize the quality of the thin film.

After the heat-processing was completed, an electrode 2 as shown in FIGS. 1A and 1D was formed through a chemical etching process. At this time, the chemical etching process with respect to the Pt electrode 2 was performed by a spin coating process for about 30 seconds at a speed of 4000~4200 rpm by using a positive photosensitive material, and then a soft bake process was performed for 15 minutes at a temperature of about 85° C. Thereafter, the resultant was exposed to He light for about 40 seconds to print the same, and then a hard bake process was performed for 30 minutes at a temperature of about 110° C., and finally an etching process was performed with respect thereto by using an etchant which was capable of removing the thin film. After the etching process was completed, the photosensitive material remaining on the Pt electrode pattern was eliminated by using a mixed solution ($H_2SO_4:H_2O_2=19:1$) of sulfuric acid and hydrogen peroxide, and then the resultant was washed by de-ionized water.

Next, in the heater fabrication process, a thick film having a predetermined pattern was formed on the back surface of the alumina substrate 1 by using a palladium-silver paste in a silk screen printing process.

In addition, in the wire connection step, a Pt lead wire was connected to the electrode and the heater, respectively. The wire was connected to the electrode 2 by using a Pt paste and was connected to the heater 4 by using a palladium-silver paste, and then the resultant was heat-processed for 10 minutes at a temperature of 850° C.

Next, in the process for fabricating a tungsten oxide thin film for sensing $NO_x$ gas, the tungsten oxide thin film was formed on the alumina substrate 1 on which the electrode 2 was formed, to a thickness of a few thousands of Å to 2 μm by using a $WO_3$ pellet in a resistance heating type vacuum deposition process. The $WO_3$ pellet was manufactured by mixing $WO_3$ powder with PVA of 10% water-solution and removing the binder of the pellet and shaping the resultant for 10 minutes at a temperature of 800° C. to provide a predetermined strength thereto.

After the $WO_3$ film 3 was deposited, the resultant was heat-processed at a temperature of 500~800° C. which was higher than the sensor sensing temperature (150~300° C.) in order to enhance and stabilize the crystallinity of the thin film.

Next, the heat-protection and insulation coating process of the gas sensor was performed by coating an alumina paste for high temperature on the palladiumsilver thick film heater.

In the catalytic layer formation step, the catalytic layer was formed on the alumina substrate 1 on which the oxide tungsten thin film was deposited, to a thickness of 1 to 100 Å by using a Ni metal in a resistance heating type vacuum deposition process or Ni or NiO target in sputtering system. After the catalytic layer was deposited, the resultant was heat-processed as in the tungsten oxide thin film in order to enhance and stabilize the crystallinity of the thin film.

$WO_3$ thin film which is a sensing thin film according to the present invention was deposited in a DC sputtering process to a thickness of about 3000 Å by using a tungsten metal target and in a state of the temperature of the substrate being maintained at 500° C. under an oxygen environment of about 20%, and then the resultant was heat-processed at a temperature of 600° C. A catalytic layer was deposited to a thickness of about 30~40 Å by using a Ni metal target at a room temperature by a DC sputtering process, and then the resultant was also heat-processed at a temperature of 600° C. for 3 minutes.

Figure 3C:
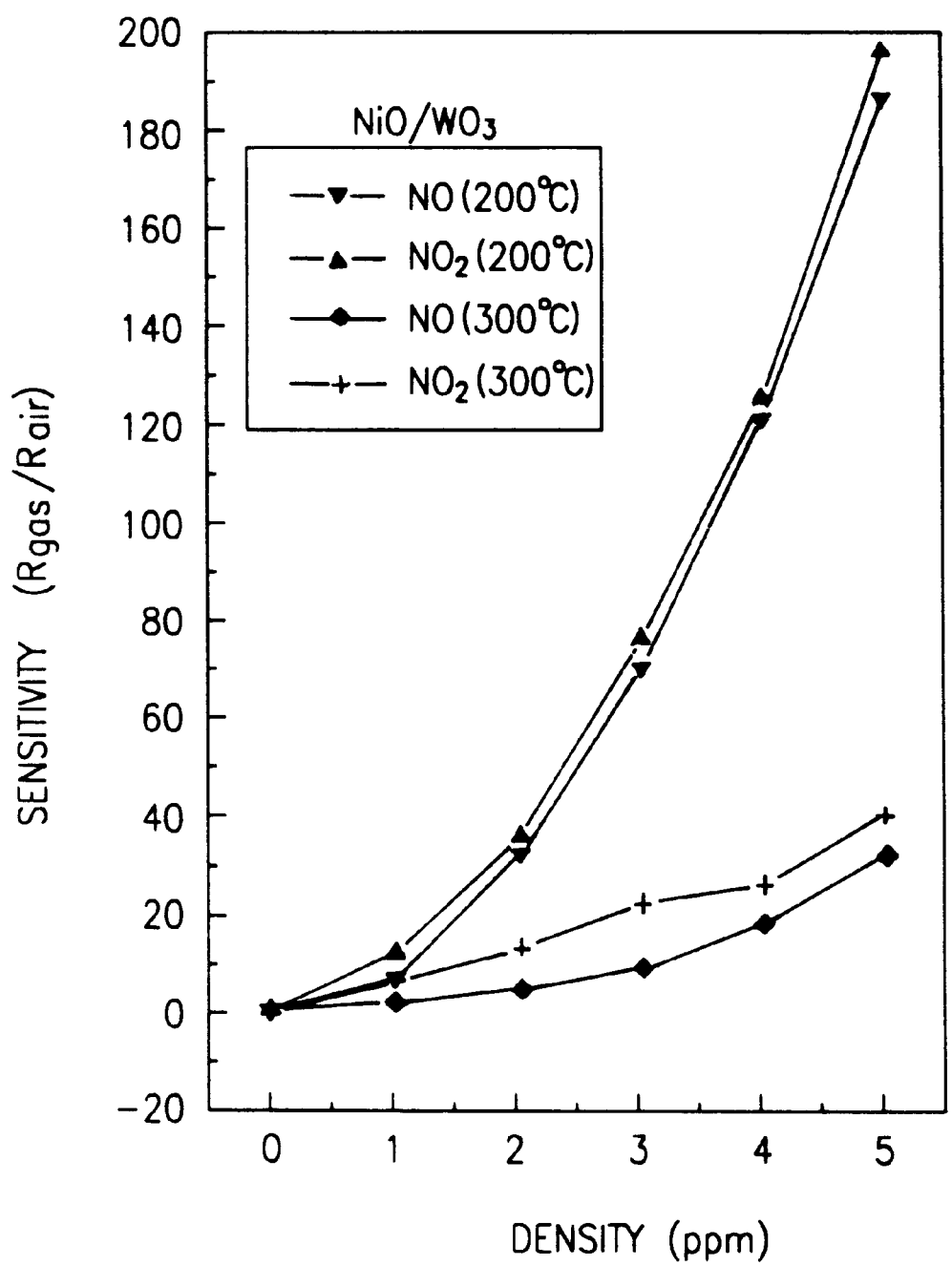

FIGS. 3A and 3C illustrate the variation of sensitivity of the gas sensor under the condition that the catalytic layer was provided or not provided in accordance with the density variation of $NO_x$ gas in a range of 1~5 ppm. As shown therein, although the sensitivity variations according to the gas density were very similar, the sensitivity of the gas sensor on which the catalytic layer was formed increased as the gas density increased. $NO_x$ gas of 5 ppm, the increase of the sensitivity by about 10% was accomplished.

Figure 4A:
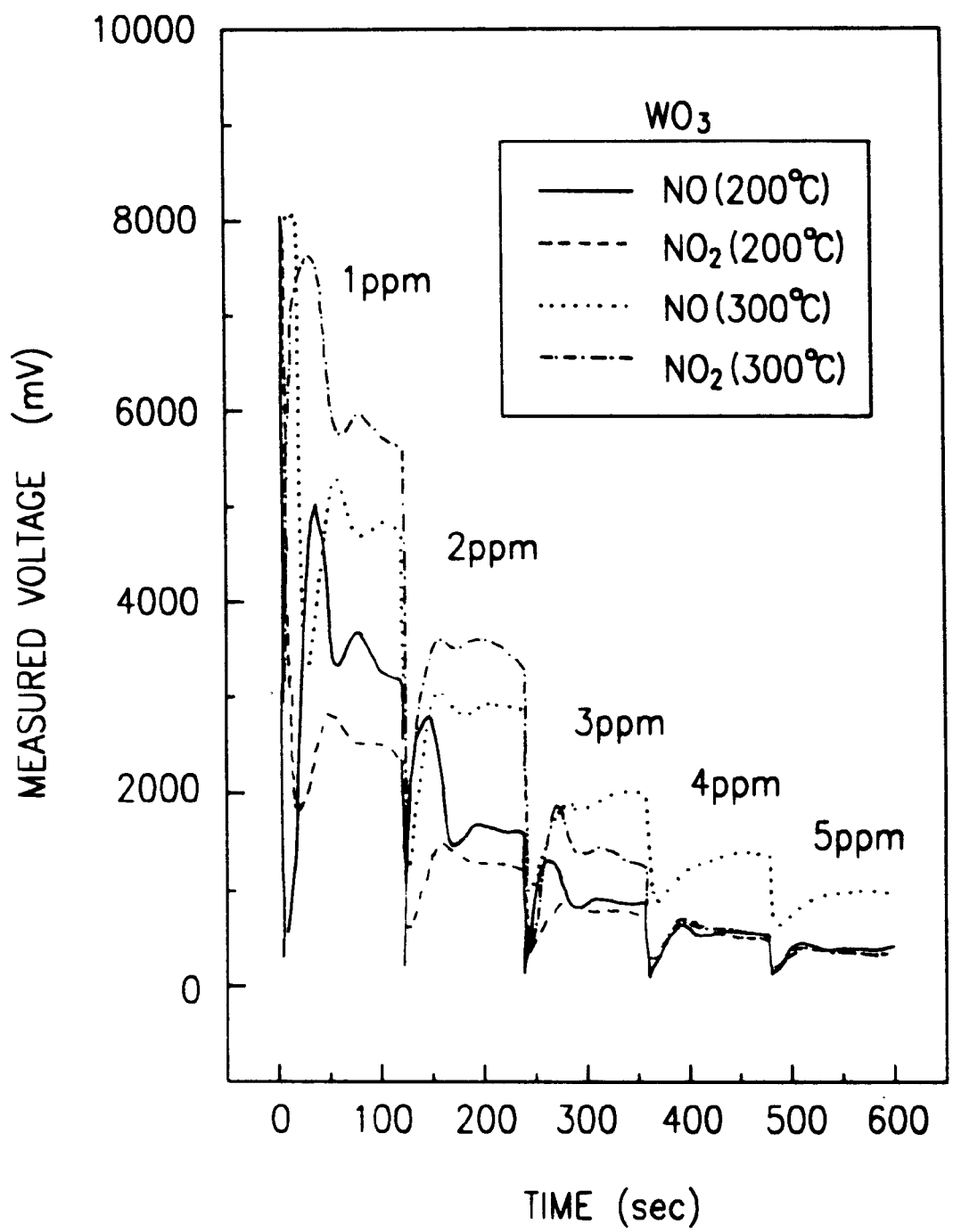
Figure 4B:
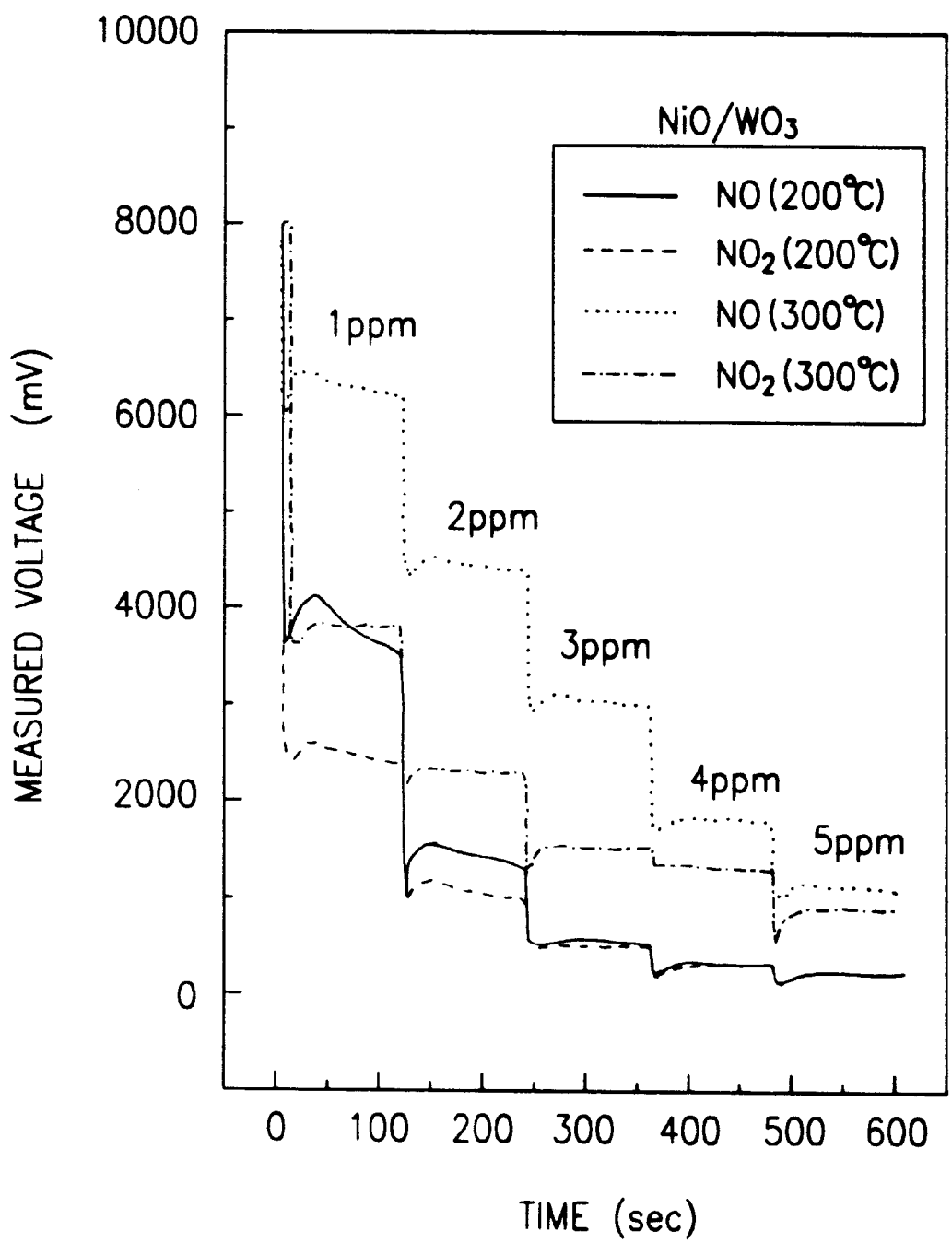

As mentioned above, FIG. 4A illustrates a response characteristics of an output voltage in each $NO_x$ gas density (1~5 ppm) measured by using a sensor including only a $WO_3$ sensing thin film. As shown therein, when the gas density was varied, the output voltage was stabilized after a time lapse of about 40~50 seconds. However, when the gas sensor was provided with a catalytic layer according to the present invention, as shown in FIG. 4B, the output voltage was stabilized within 10~30 seconds. Therefore, the catalytic layer enables a rapid electron transfer between the measured gas and the sensitive thin film.

As described above, in the $NO_x$ gas sensor having a $WO_3$ sensing film and a fabrication method thereof according to the present invention, it is possible to fabricate a high sensitive $NO_x$ gas sensor at low cost. In addition, the $NO_x$ gas sensor is applicable to measuring gas exhausted from vehicles.

Although the preferred embodiments of the present invention have been disclosed for illustrative purposes, those skilled in the art will appreciate that various modifications, additions and substitutions are possible, without departing from the scope and spirit of the invention as recited in the accompanying claims.

What is claimed is:

1. A bar-type $NO_x$ gas sensor having a $WO_3$ sensing film, comprising:

an alumina bar having a certain diameter made of a material selected from the group consisting of alumina, mullite, cordierite, magnesia and zirconia;

a heater formed on the alumina bar;

a sheet made of a material selected from the group consisting of alumina, mullite, cordierite, magnesia and zirconia covering the heater;

a Pt thin film electrode formed on the sheet; and a tungsten oxide thin film for sensing $NO_x$ gas formed on the Pt thin film electrode wherein the sheet is at least 1 mm in thickness.

2. The $NO_x$ gas sensor of claim 1, wherein further comprising a catalytic layer deposited on the tungsten oxide thin film.

3. The $NO_x$ gas sensor of claim 2, wherein said catalytic layer is formed of NiO.

4. The $NO_x$ gas sensor of claim 1, wherein said heater is made of tungsten paste.

5. The $NO_x$ sensoring of claim 1, wherein the diameter of the alumina bar is 5–10 mm.

* * * * *